US 6,743,937 B2

(12) United States Patent
Seyedi et al.

(10) Patent No.: US 6,743,937 B2
(45) Date of Patent: Jun. 1, 2004

(54) EFFICIENT METHOD OF SYNTHESIZING COMBRETASTATIN A-4 PRODRUGS

(75) Inventors: Faye Seyedi, Canton, MA (US); Jonathan Gale, W. Townsend, MA (US); Reem Haider, Lexington, MA (US); John Hoare, Lunenburg, MA (US); Amy Baldwin, Belmont, MA (US)

(73) Assignee: OxiGene, Inc., Watertown, MA (US)

( * ) Notice: Subject to any disclaimer, the term of this patent is extended or adjusted under 35 U.S.C. 154(b) by 0 days.

(21) Appl. No.: 09/908,321

(22) Filed: Jul. 17, 2001

(65) Prior Publication Data

US 2002/0119951 A1 Aug. 29, 2002

Related U.S. Application Data

(60) Provisional application No. 60/218,766, filed on Jul. 17, 2000.

(51) Int. Cl.[7] .................................................. C07F 9/09
(52) U.S. Cl. ....................................................... 558/210
(58) Field of Search ........................................ 558/210

(56) References Cited

U.S. PATENT DOCUMENTS

| 4,996,237 A | 2/1991 | Pettit et al. ................ 514/720 |
| 5,561,122 A | 10/1996 | Pettit et al. ................ 514/130 |
| 5,569,786 A | 10/1996 | Pettit et al. ................ 568/646 |

FOREIGN PATENT DOCUMENTS

| WO | 9216486 | 10/1992 |
| WO | 9935150 | 7/1999 |

OTHER PUBLICATIONS

G.R. Pettit et al., "Antineoplastic Agents. 291. Isolation and Synthesis of Combretastatins A–4, A–5 and A–6," *J. Med. Chem.* 38:1666–72 (1995).

G.R. Pettit et al., "Antineoplastic Agents 389. New syntheses of the combretastatin A–4 prodrug," *Anti–Cancer Drug Design* 13:183–91 (1998).

*Primary Examiner*—Joseph K. McKane
*Assistant Examiner*—Rebecca Anderson
(74) *Attorney, Agent, or Firm*—Barry J. Marenberg, Esq.; Ivor R. Elrifi, Esq.; Mintz, Levin, Cohn, Ferris, Glovsky and Popeo, P.C.

(57) ABSTRACT

Methods of synthesizing a phosphate ester of combretastatin A-4 and trans-isomers thereof in which combretastatin A-4 is reacted with dibenzylphosphite in the presence of carbon tetrabromide, or with 2,2,2-trichloroethyl phosphorodichloridate, to form a phosphate ester of combretastatin A-4 with protecting groups thereon.

32 Claims, 5 Drawing Sheets

EFFICIENT METHOD OF SYNTHESIZING COMBRETASTATIN A-4 PRODRUGS

CROSS REFERENCE TO RELATED APPLICATION

This application claims the priority benefit, under 35 U.S.C. §119(e) (1), of applicants' U.S. provisional application No. 60/218,766, filed Jul. 17, 2000, the entire disclosure of which is incorporated herein by this reference.

BACKGROUND OF THE INVENTION

The present invention relates generally to the field of compounds with antiangiogenesis effects that may be useful in the treatment of one or more neoplastic diseases.

In particular, the present invention relates to new and efficient methods of synthesizing prodrugs of the known antiangiogenesis compound denominated combretastatin A-4 and its analogs as described in U.S. Pat. Nos. 4,940,726; 5,409,953; and 5,569,786. More particularly, this invention relates to the improved and efficient phosphorylation and deprotection of phenol combretastatin A-4 in the synthesis of water soluble antiangiogenesis prodrugs of combretastatin A-4.

Combretastatin A-4 (Formula 1 below) is reported to be an antineoplastic compound inhibiting cancer cell growth and tubulin assembly.

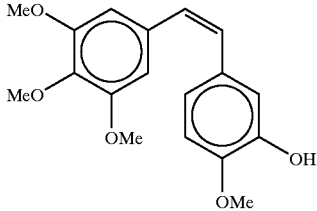

(1)

It is believed that combretastatin A-4 attacks the lining of blood vessels that grow around tumors, thereby severing the blood supply to the cancerous tumor. Although combretastatin A-4 has exhibited strong anti-cancer activity, its development has been inhibited by extremely poor solubility in water making development and biological distribution impracticable.

Water-soluble prodrug derivatives of combretastatin A-4 have been reported recently. In particular, synthesis of phosphate salts of combretastatin A-4, designated "combretastatin A-4P" (Formula 2 below) have been found to impart the requisite water solubility to the prodrug and are disclosed in U.S. Pat. No. 5,561,122 issued to G. R. Pettit et al. on Oct. 1, 1996. The phosphate group of the prodrug combretastatin A-4P reportedly is hydrolyzed in vivo to liberate the active drug combretastatin A-4. However, the currently disclosed methods for synthesizing combretastatin A-4P are difficult, require the use of undesirable solvents or restricted solvents, and are not easily scalable.

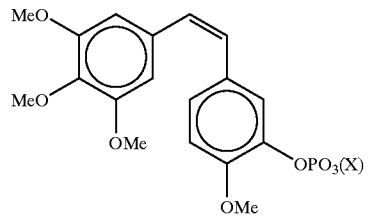

(2)

where X=H(Z) (monovalent) or X=Z (divalent),
Z=$Na^{2+}$, $Na^+$, $Li^+$, $Mg^{2+}$, $Mn^{2+}$, $Zn^{2+}$, $Ca^{2+}$, $Cs^{2+}$, imidazol morpholine, piperazine, piperidine, pyrazole, pyridine, adenosine, cinchonine, glucosamine, quinine, quinidine, tetracycline, verapamil.

An improved method of preparing prodrugs of combretastatin is, necessary in order to meet the demand for an efficient and scalable synthesis to produce combretastatin A-4P and isomers thereof for effective use in treating cancer tumors and similar diseases.

SUMMARY OF THE INVENTION

It is an object of the present invention to synthesize prodrugs of combretastatin A-4 that are both water soluble and stable. It is a further object of the invention to develop an efficient and scalable method for synthesizing cis- and trans-prodrugs of combretastatin A-4.

Although combretastatin A-4 is a potent anticancer agent, its poor water solubility has hindered development of the drug as an anticancer treatment. Current methods of synthesizing water soluble derivatives of combretastatin A-4 require the use of undesirable or restricted solvents, such as chloroform, pyridine, dichloromethane or dimethylformamide ("DMF"), require extractions, separations and dilution of the reaction solutions, and heating and cooling of reaction mixtures at temperatures that are not suitable for production of prodrugs of combretastatin A-4 in commercial quantities.

As detailed herein, the subject invention provides a novel and improved method of synthesizing combretastatin A-4P that minimizes or eliminates the use of undesirable solvents, and overcomes many other deficiencies of the prior art using a continuous process. A novel process is herein disclosed in which dibenzyl phosphite/carbon tetrabromide is used to phosphorylate phenol combretastatin A-4 forming a phosphate ester of combretastatin A-4 with benzyl protecting groups thereon. An improved method of cleaving the benzyl protecting groups from the phosphate ester of combretastatin A-4 is disclosed in which bromotrimethylsilane is reacted with combretastatin A-4 to form phosphoric acid of combretastatin. An alternate novel phosphorylation process was concurrently developed and is herein disclosed in which bis(2,2,2-trichloroethyl) phosphorodichloridate phosphorylates combretastatin A-4 to a phosphate ester with trichloroethyl protecting groups thereon. The trichloroethyl groups are then cleaved from combretastatin A-4 using Zn/Cu amalgam to form a phosphoric acid of combretastatin A-4. Further improvements to the current processes for synthesizing phosphate salts of combretastatin A-4 are described herein disclosing a continuous process that overcomes many obstacles and limitations to the use and large scale production of combretastatin A-4 prodrugs.

In another aspect, the invention embraces the provision of combretastatin A-4 prodrug products of the aforesaid novel and improved method.

In a further aspect, the invention contemplates the provision of methods of synthesizing combretastatin A-4 prodrugs including a complete procedure for synthesizing cis combretastatin A-4, to which the foregoing method steps and procedures may then be applied to obtain the prodrug. The procedure for synthesizing cis combretastatin A-4 in accordance with this aspect of the invention includes the steps of obtaining a phosphonium salt of 3,4,5-trimethoxybenzyl bromide by mixing a brominating reagent and 3,4,5-trimethoxybenzyl alcohol in toluene to obtain the bromide, and adding triphenylphosphine thereto; obtaining tritylated isovanillin by mixing an amine base, isovanillin, and trityl chloride in an ether solvent, and after quenching, adding heptane and ethyl acetate; mixing a suspension of the phosphonium salt in tetrahydrofuran, an alkyl lithium reagent, and a slurry of the tritylated isovanillin, to obtain a cis/trans stilbene; and reacting the cis/trans stilbene with an acid to obtain a product consisting essentially of cis combretastatin A-4.

As in other embodiments of the invention, a combretastatin A-4 prodrug may then be prepared from the latter product by reacting the cis combretastatin A-4 with an activated phosphorylating agent having hydroxyl-protecting groups thereon wherein the phosphorylating agent is either dibenzylphosphite/carbon tetrabromide or bis(2,2,2-trichloroethyl) phosphorochloridate, to form a phosphate ester of combretastatin with protecting groups thereon; deprotecting the hydroxyl-protecting groups with a deprotecting agent to yield a phosphoric acid of combretastatin A-4; and reacting the phosphoric acid with reactive agent to form a phosphate salt of combretastatin A-4.

In the combretastatin A-4 synthesis procedure described above, it is currently preferred that the brominating reagent is phosphorus tribromide, the triphenylphosphine is unsubstituted triphenylphosphine, the amine base is triethyl amine, the ether solvent is tetrahydrofuran, the trityl chloride is unsubstituted trityl chloride, the alkyl lithium reagent is n-butyl lithium, and the acid is hydrochloric acid.

Further features and advantages of the invention will be apparent from the detailed description hereinafter set forth, together with the accompanying drawings.

DETAILED DESCRIPTION

Figure 1:
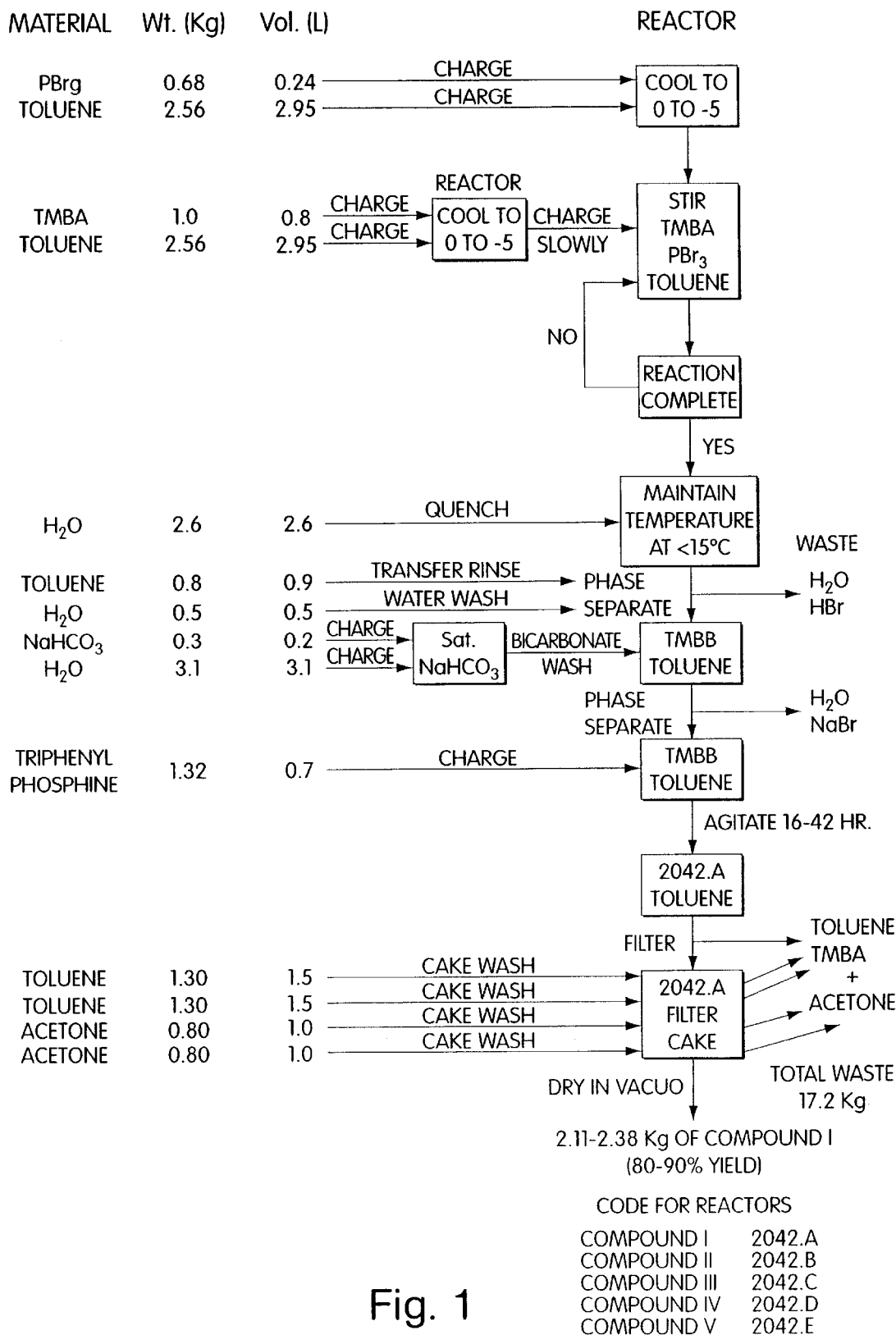
FIG. 1 is a flow chart illustrating the first step in a specific example of the complete synthesis of a combretastatin A-4 prodrug in an embodiment of the method of the invention.

The elucidation and isolation of combretastatin A-4 are described in U.S. Pat. No. 4,996,237 which issued to G. R. Pettit et al., on Feb. 26, 1991, while early efforts to develop a combretastatin A-4 prodrug are described in U.S. Pat. No. 5,561,122, which issued to G. R. Pettit on Oct. 1, 1996. The general background information from each of those patents is incorporated herein by reference. The subject invention presents a novel method of synthesizing prodrugs of combretastatin A-4. More specifically, the present invention provides novel methods of phosphorylation and deprotection in the synthesis of prodrugs of combretastatin A-4.

Troc Phosphorylation—Prior Synthetic Methods

Existing methods of preparing prodrugs of combretastatin A-4 using a bis(2,2,2-trichloroethyl) phosphorodichloridate ("Troc") protected phosphorylating group contain many deficiencies (the "Troc Method"). While current Troc Methods vary slightly, a detailed synthesis of combretastatin A-4 prodrug as illustrated in Formula 3 is representative of a method of synthesizing combretastatin A-4 using Troc Phosphorylation. The Troc Method requires the use of neat pyridine, a toxic solvent with a high boiling point making product isolation difficult, and requiring stripping the solvent/reagent in the initial phosphorylation step. Further, the Troc Method requires the use of carcinogenic chloroform in the initial phosphorylation reaction. Moreover, phosphorylation by this method requires the use of dimethylformamide having a high boiling point of 153° C. Use of DMF necessitates the additional step of evaporating the solvent during deprotection of the phosphoric ester. The Troc Method requires the use of Zn/Cu amalgam to deprotect the intermediate of the Troc group, leaving heavy metal contaminants that are difficult to remove from the final product. Further steps that are involved in the Troc Method include the use of an ion exchange column and the subsequent evaporation of a large volume of solvent, extended refrigeration for crystallization of intermediates, evaporation of the solvents to dryness in both steps, chemical drying of the chloroform solution of the protected phosphorylated product, and isolation of the protected phosphorylated combretastatin A-4 prodrug product. Contributing to these time consuming and costly steps, the Troc Method requires all reactions be performed at high dilution and isolation by ion-exchange chromatography or similar means, further increasing the time and cost of isolating the combretastatin A-4 prodrug and its intermediates by this method and limiting this method to small scale production.

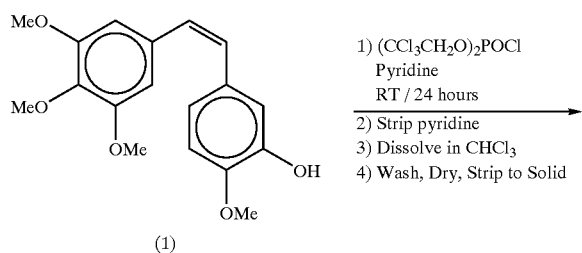

(1)

(3)

1) (CCl₃CH₂O)₂POCl
   Pyridine
   RT / 24 hours
2) Strip pyridine
3) Dissolve in CHCl₃
4) Wash, Dry, Strip to Solid -continued

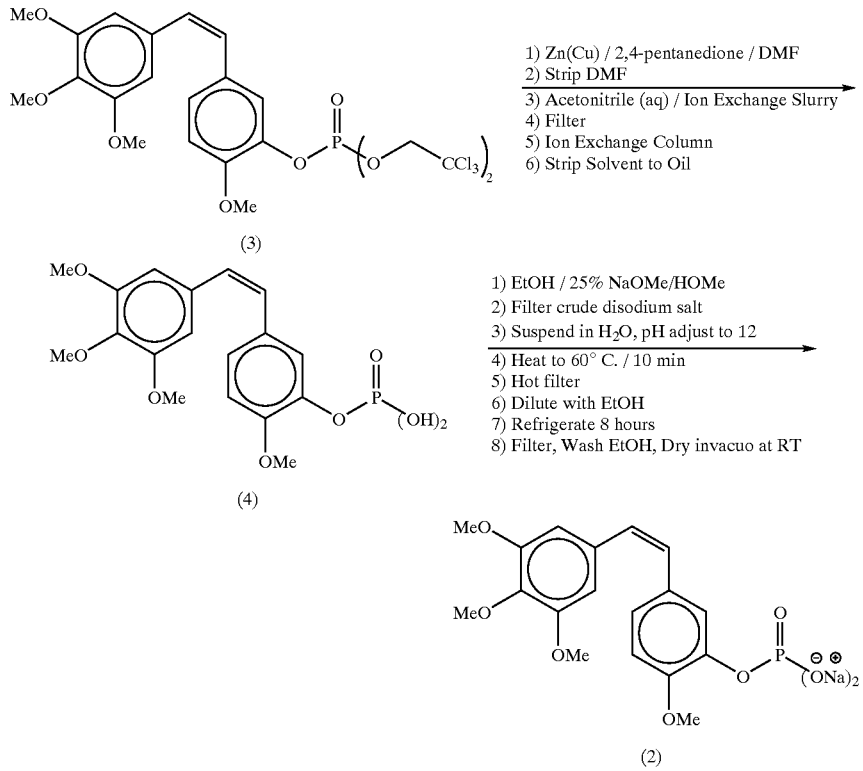

The difficulties with existing phosphorylation methods in the synthesis of combretastatin A-4P were investigated and a novel was efficient synthesis of prodrugs of combretastatin A-4 was developed that substantially reduced the cost and time required to synthesize combretastatin A-4P. Table 1 summarizes the developments that were made to improve upon the current phosphorylation methods described above.

TABLE 1

Summary of Improvements to Troc Phosphorylation Method

| Entry | Improvements | Result |
| --- | --- | --- |
| 1 | Replacement of pyridine with triethylamine in phosphorylation | Reaction proceeded faster and gave white solid of combretastatin A-4P |
| 2 | Replace DMF with Acetonitrile Isolate intermediate Phosphate Acid of combretastatin A-4 | 71% crude yield 46% recrystalization 98.3 wt % Assay |
| 3 | No isolation of intermediate Phosphate Acid of combretastatin A-4 | 88% crude yield 41% recrystalization 95.5 wt % Assay |
| 4 | Recrystalization of combretastatin A-4P from acetonitrile/water | Scaleable recrystalization developed 66% recovery from Entry 1 final product |

Novel Synthetic Method with Troc Phosphorylation

The first improvement to the existing Troc Method was the replacement of neat pyridine with triethylamine ("TEA") and a reactive amount of dimethylaminopyridine ("DMAP") (Table 1, Entry 1). The reaction proceeds much more rapidly with TEA than with pyridine (1.5 hours vs. 16 hours). Replacing the DMF solvent (boiling point of 152.8° C.) with acetonitrile (boiling point 82° C.) (Table 1, Entry 2) was still a further improvement making isolation of the product from solvent easier to perform. The phosphate ester intermediate having Troc protecting groups thereon may then be deprotected without the need for isolation. Deprotection of the intermediate is performed using acetonitrile in Zn/Cu amalgam to form the intermediate phosphate acid of combretastatin A-4P.

The intermediate phosphate acid is isolated using a Dowex™ ion-exchange resin, purchased from Aldrich Chemical Company, Milwaukee, Wis., and thereby eliminating the need for separation by chromatography. Alternatively, synthesis may be performed without isolation of the intermediate phosphate acid (Table 1, Entry 3) to produce product with low Zn/Cu levels (130 ppm) thereby limiting the cis/trans isomerization of intermediates caused by such metals.

The improvements to the Troc phosphorylation method of the subject invention overcome the problems attributable to the Troc method disclosed in the prior art, resulting in a new and improved phosphorylation method to synthesize the combretastatin A-4P using Troc as a protecting group to form 3'-O-Bis-2,2, 2-(trichlorethyl) phosphate combretastatin A-4 (5). See Formula 4.

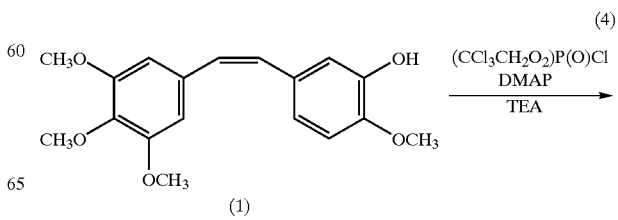

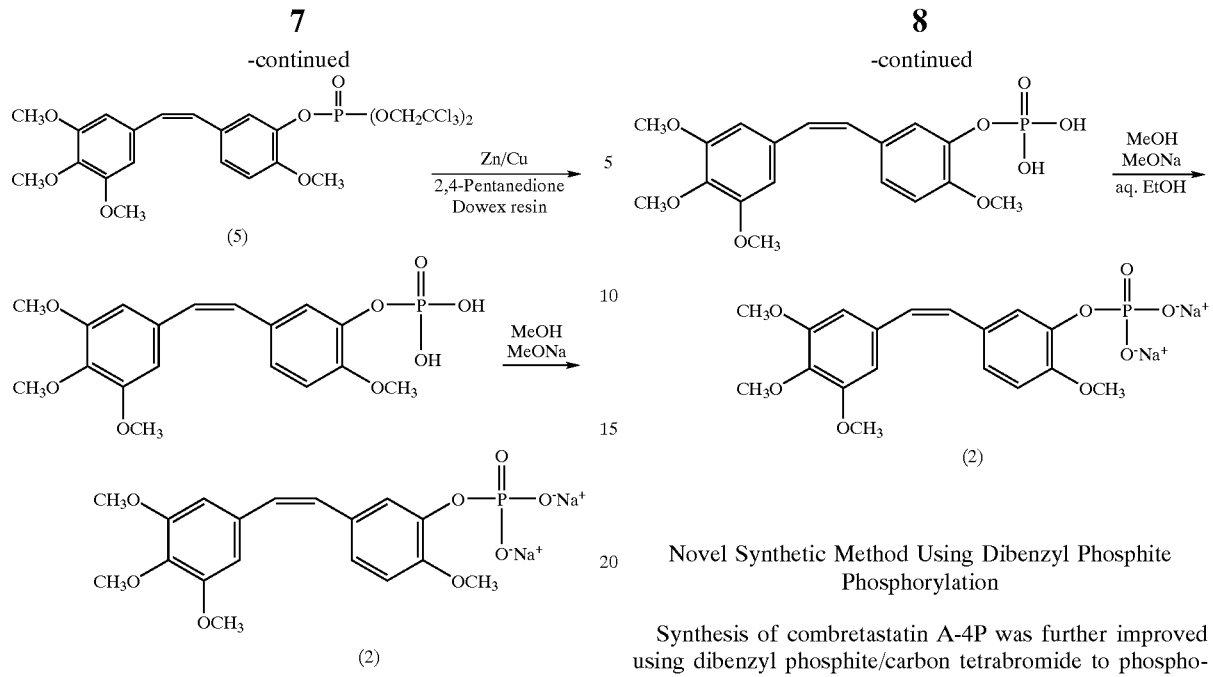

Benzyl Phosphorylation—Prior Methods

An alternate phosphorylation method is described in international patent application PCT/US99/00419, by Pettit, G. R. et al. filed Jan. 8, 1999, describing the use of dibenzyl phosphite/carbon tetrachloride to phosphorylate the phenol combretastatin A-4 with benzyl protecting groups thereon and deprotecting the intermediate using iodotrimethylsilane ("TMS-I") (the "Benzyl-I Method") . See Formula 5. However, this method requires the use of undesirable solvents and reagents such as chloroform, chlorotrimethylsilane/sodium iodide, and iodotrimethylsilane, which leave impurities that catalyze the conversion of cis isomers of combretastatin A-4P to the trans isomer resulting in product that is not optically pure. Further, these undesirable solvents and reagents are highly toxic and use in the synthesis necessitates lengthy heating and cooling reactions. These as well as other problems with the Benzyl-I Method have been overcome by the subject invention.

Novel Synthetic Method Using Dibenzyl Phosphite Phosphorylation

Synthesis of combretastatin A-4P was further improved using dibenzyl phosphite/carbon tetrabromide to phosphorylate the phenol combretastatin A-4 (Formula 1) with benzyl protecting groups thereon to form 3'-O-Bis(benzyl) phosphate combretastatin A-4. See Formula 6.

Table 2 summarizes the improvements to the synthetic processes of the prior art by use of the dibenzyl phosphite/carbon tetrabromide phosphorylation method.

The combretastatin A-4 is phosphorylated using dibenzyl phosphite in presence of triethylamine, carbon tetrabromide, and DMAP, and dibenzylphosphite in acetonitrile to yield crude 3'-O-Bis(benzyl)phosphorylcombretastatin A-4. See (6) in Formula 6. These improvements to the benzyl phosphorylation reaction cause the reaction to go to completion leaving only trace phenol combretastatin (I). Further improvements to the process resulted in the elimination of the use of DMAP in the reaction, which is a difficult solvent to remove from the product due to its high boiling point. The crude product is isolated and debenzylation of 3'-O-Bis (benzyl)phosphorylcombretastatin A-4 product is performed using bromotrimethylsilane ("TMS-Br") in acetonitrile. The capricious nature of the deprotection of the benzyl groups from the phosphate ester was observed in Pettit Patent App. PCT/US99/00419. Initial debenzylation experiments yielded only trans product as determined by HPLC/UV analysis (Table 2, Entry 1). Addition of 0.1 eq of NaHCO₃ gave a 50:50 mixture of the cis and trans product (Entry 2). No improvement in the ratio of intermediate isomers was noted when 1 equivalent of NaHCO₃ was used (Entry 3). The TMS-Br reaction with the addition of 1 equivalent of Hunnings base gave only trans product (Entry 4). The TMS-I (stabilized with Cu metal) reaction also gave only trans product (Entry 5).

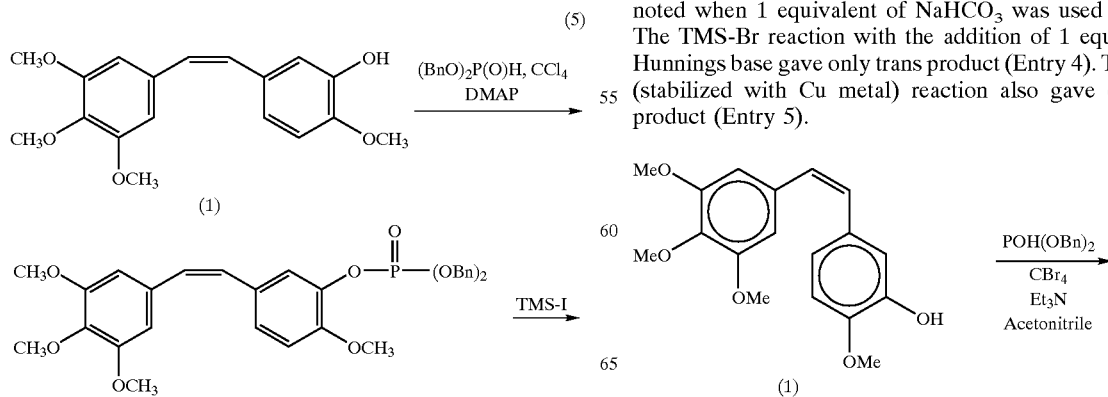

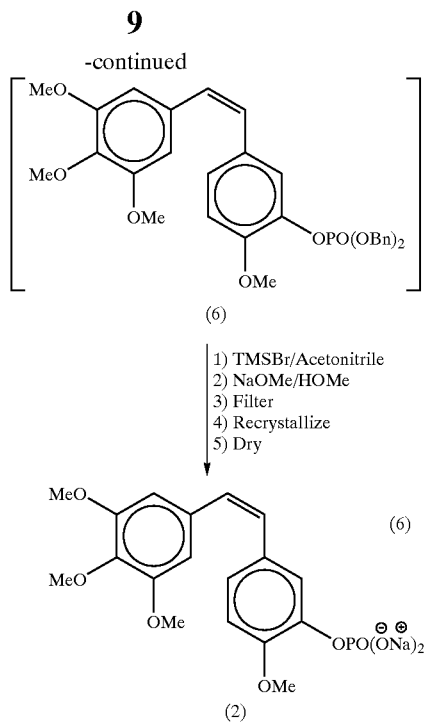

methoxide in methanol and allowed to stir, preferably overnight. The crude all cis product is filtered out (Entry 7) in approximately 75% yield from cis-combretastatin A-4. In experimental results, the reported w/w assay of the combretastatin A-4P product was 81.4% desired (Entry 8). Since no impurities were observed in $^1$H NMR and HPLC it was concluded that the impurities were predominantly inorganic salts.

In order to remove impurities, crude combretastatin A-4P may be stirred into water/methanol mixture and the solution basified to pH 10–12 resulting in the crude product to become completely dissolved in solution. The mixture is then heated to "approximately 35–40° C. for about one hour.

Acetone is added to the solution and allowed to cool to room temperature before a second volume of acetone was added. The material is then stirred overnight and the product filtered out. The experimental variations in solvent volume to gram of material are described in Table 3. Optimal results were obtained by recrystalizing the crude combretastatin A-4P material ("Product") with a mixture of water/methanol/acetone (5/5/10 ml/g crude) yielding in 40% recovery from starting phenol combretastatin A-4 (Entry 4).

TABLE 3

Summary of Purification Methods

| Entry | Improvements | Result |
|---|---|---|
| 1 | Recrystalization of combretastatin A-4P water/methanol/ acetone (mL/g solid) 4/4/8 | wt/wt 97.2%, pH 7.98, Na 16%, KF 3.6%, Recovery 48% |
| 2 | Trituration of CA-4P 10% H$_2$O/Acetone | wt/wt 98.1%, pH 7.59, Na 16%, KF 4.1%, Recovery 43% |
| 3 | Trituration of CA-4P 20% H$_2$O/Acetone | wt/wt 100.6%, pH 7.53, KF 12%, Recovery 29% |
| 4 | Recrystalization of CA-4P water/methanol/ acetone (mL/g solid) 5/5/10 | wt/wt 98.8%, pH 8.65, Na 10.1%, KF 2.9%, Recovery 40% |
| 5 | Recrystalization of CA-4P water/methanol/ acetone (mL/g solid) 6/5/10 | wt/wt 99.1%, pH 8.81, Na 10.1%, KF 5.28%, Recovery 23% |
| 6 | Trituration of CA-4P 20% H$_2$O/Acetone | wt/wt 98%, KF 2.87%, Recovery 43% |

While the invention as described above embraces methods of synthesizing prodrugs of combretastatin A-4 regardless of how the combretastatin A-4 itself is obtained or prepared, in a further sense the invention also contemplates complete methods of producing combretastatin A-4 prodrugs including a preferred synthesis of combretastatin A-4 followed by phosphorylation and deprotection to provide the prodrug. An embodiment of such a complete method in accordance with the invention will now be set forth.

Synthesis of Combretastatin A-4
Step 1 (Preparation of the Phosphonium Salt)

A cold solution of a brominating reagent in toluene is added to a cold solution of 3,4,5-trimethoxybenzyl alcohol (TMBA) in toluene and the mixture is stirred until the reaction is complete. The brominating reagent currently preferred is phosphorus tribromide (PBr$_3$); examples of alternative brominating reagents include gaseous HBr, triphenylphosphine dibromide and SOBr$_2$. The resulting bromide (TMBB) is quenched with water and washed. The phases are separated and triphenylphosphine (Ph$_3$P) is added to the organic phase. As used herein, the term "triphenylphosphine" includes unsubstituted triphenylphosphine, which is currently preferred for this step, and singly or multiply

TABLE 2

Summary of Benzyl Phosphorylation Method

| Entry | Method of Improvements | Result |
|---|---|---|
| 1 | TMS-Br (Aldrich)/Acetonitrile | 98+% trans isomer formed |
| 2 | TMS-Br/NaHCO$_3$ 0.1 eq | 50/50 cis/trans |
| 3 | TMS-Br/NaHCO$_3$ 1 eq | 50/50 cis/trans |
| 4 | TMS-Br/Hunnings Base | trans |
| 5 | TMS-I/Cu stabilized | trans |
| 6 | Distilled TMS-Br | cis |
| 7 | Distilled TMS-Br Continuous process | Shorter reaction time, no solvent evaporation |
| 8 | Dibenzyl route Continuous process | wt/wt 81.4%, Na 13%, KF 2.95%, recovery 76% |

Hydrolysis of the combretastatin A-4 phosphate ester with aqueous Na$_2$CO$_3$ gave no reaction. Since the HPLC of 3'-O-Bis(benzyl)phosphate combretastatin A-4 did not show the presence of any trans isomer, the transformation from cis to trans was apparently catalyzed by trace I$_2$, Br$_2$, or HBr impurity. Using distillated TMS-Br (Aldrich, slightly orange) under N$_2$ atmosphere resulted in debenzylation of the phosphate ester with no noted isomerization of the cis product (Entry 6). This improvement to the debenzylation reaction overcame the need for time-consuming and costly factions and recrystallization procedures to isolate pure isomers of the phosphoric acid of combretastatin A-4.

The phosphorylation and debenzylation steps were further developed into a continuous process. Phenol combretastatin A-4 is dissolved in acetonitrile and triethylamine ("TEA") and CBr$_4$ is added. The reaction mixture is cooled to 0° C. before adding dibenzylphosphite in acetonitrile. The reaction proceeds for approximately one hour. Completion of the reaction may be verified by TLC and/or HPLC. Distilled bromotrimethylsilane is then added to the same mixture. Colorless bromotrimethylsilane may be purchased from Fluka for successful debenzylation of 3'-O-Bis(benzyl) phosphate combretastatin A-4. After debenzylation, approximately 30–45 minutes to run reaction to completion, the reaction is then quenched with a solution of 25w % sodium substituted triarylphosphines

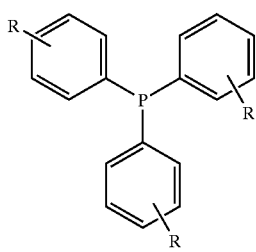
(7)

in which the group(s) attached to the aryl ring(s) in the phosphine may be lower alkyl, lower alkoxy, fluorine and nitro, the substitution pattern on the ring(s) being any location other than the carbon-phosphorus bond; the triphenylphosphine of Formula (7) is unsubstituted when all R are H.

The mixture is stirred and the solid is collected, washed and dried to provide the phosphonium salt, Compound I. Step 1 is represented as follows:

Preparation of the phosphonium salt required for the Wittig reaction

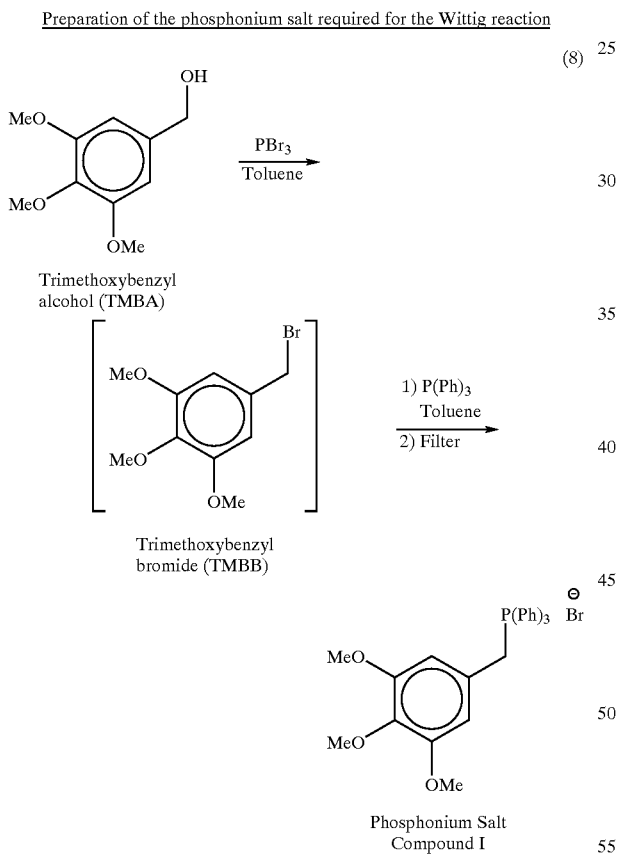
(8)

and a flow chart of a specific example is shown in FIG. 1.

Step 2 (Trityl Protection of Isovanillin)

An amine base is combined with 3-hydroxy-4-methoxybenzaldehyde (isovanillin), triphenylmethyl chloride (trityl chloride or TrCl) and an ether solvent, and the mixture is stirred with heating until the reaction is complete. The amine base is preferably triethyl amine (Et$_3$N); more generally, the amine base may be a trialkyl amine base (lower alkyl or cyclic, including aryl, up to six carbons per alkyl group or ring, examples being Ph$_3$N, R$_3$N, and cyclic amines such as pyridine, N-methyl morpholine, and DBU), or an amine resin (such as polyvinyl pyridine or IRA-68 or equivalent). As used herein, the term "trityl chloride" includes unsubstituted trityl chloride, which is currently preferred for this step, and singly or multiply (one to five groups) substituted aryl groups on the trityl chloride; the group(s) attached to the aryl ring in the trityl chloride may be lower alkyl, lower alkoxy, fluorine and nitro, the substitution pattern on the ring being any location other than the carbon-carbon bond forming the trityl chloride:

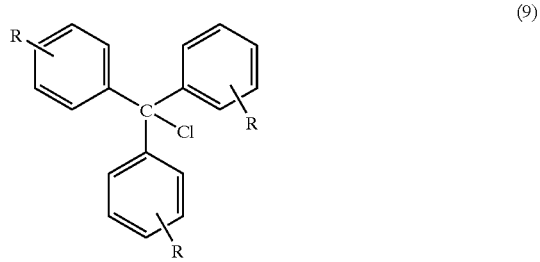
(9)

In formula (9), when R is H the trityl chloride is the currently preferred unsubstituted trityl chloride. The ether solvent may be lower alkyl or cyclic (including aryl) up to six carbons per alkyl group or ring, the preferred solvent being tetrahydrofuran (THF), other illustrative examples including Et$_2$O, dibutyl ether, methyl THF, MTBE, and dioxane. The reaction is quenched with water, and a mixture of heptane and ethyl acetate (EtOAc) is added. The mixture is stirred and the solid is collected, washed and dried to provide the tritylated hydrovanillin (Compound II). Step 2 is represented as follows:

Preparation of the protected hydroxy aldehyde for the Wittig reaction

Figure 2:
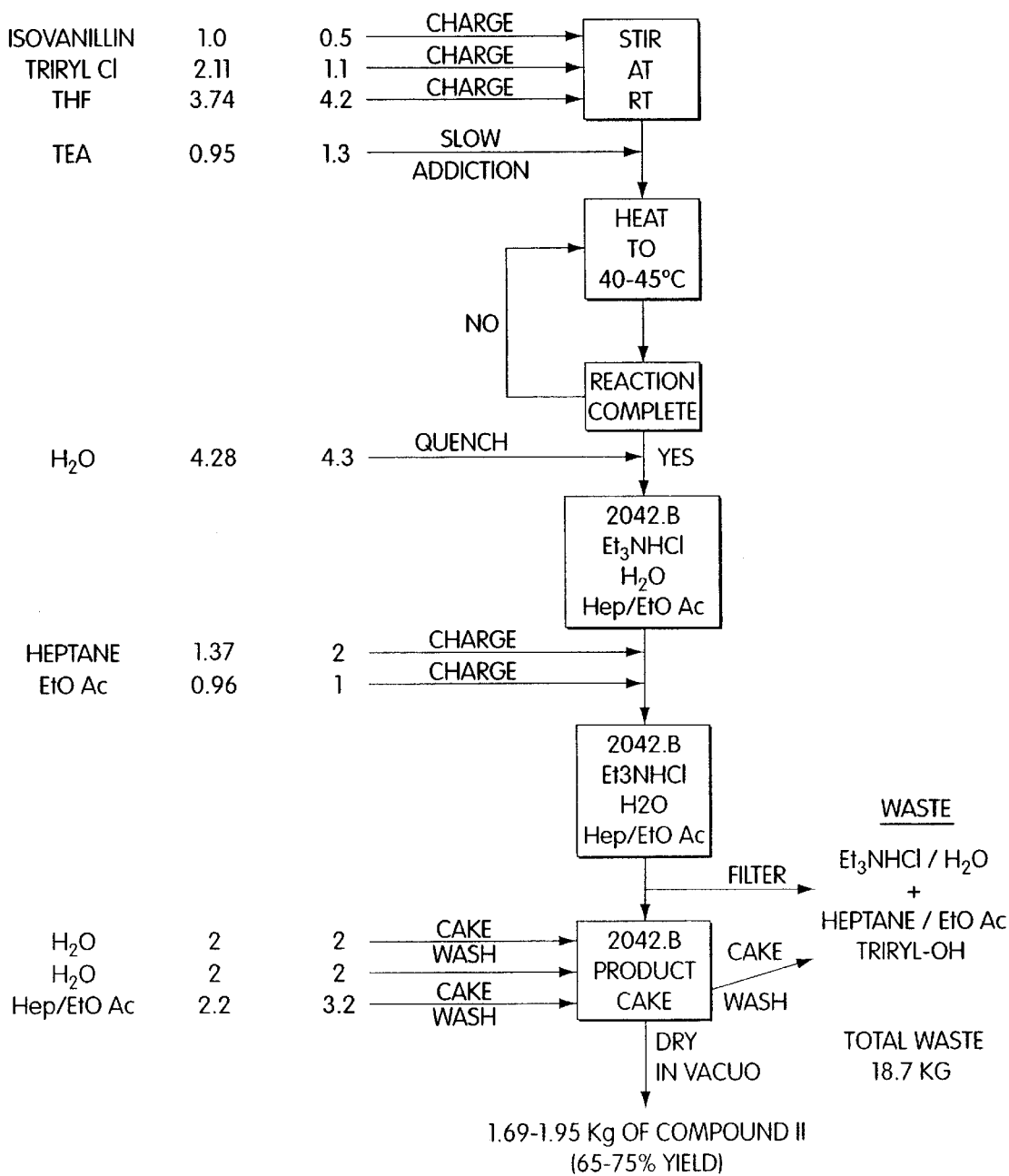
FIG. 2 is a flow chart illustrating the second step in the aforesaid specific example.

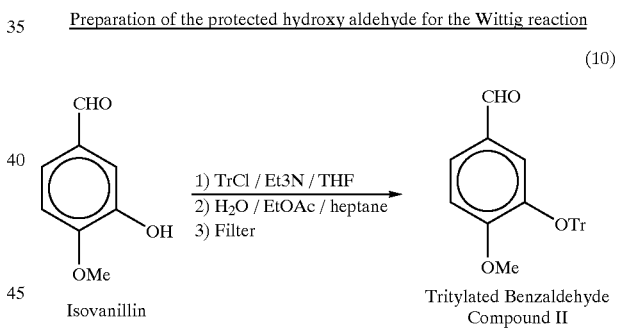
(10)

and a flow chart of a specific example is shown in FIG. 2.

Step 3 (Preparation of Cis/Trans Product by Wittig Reaction)

To a (preferably cold) suspension of the phosphonium salt (Compound I) in THF is added n-butyl lithium (n-BuLi) followed by a slurry of Compound II in THF. Alternatives to n-BuLi include other alkyl amine bases such as methyl lithium, s-butyl lithium, tert-butyl lithium, other commercially available alkyl lithium reagents such as pentyl, hexyl and octyl lithium (available from FMC LithCo Div), and hindered amine bases such as lithium diisopropyl or dicyclohexyl amide and lithium hexamethyl disilazane. The resulting mixture is stirred until the reaction is complete. The reaction is quenched with brine at a cool temperature and the phases are separated. The organic phase is partially concentrated and diluted with ethanol. The resultant slurry is stirred and cooled, and the product is collected, washed and dried to provide a cis/trans-stilbene (Compound III), in which the ratio of cis (Z) to trans (E) is 60–75% cis to 40–25% trans. Step 3 is represented as follows:

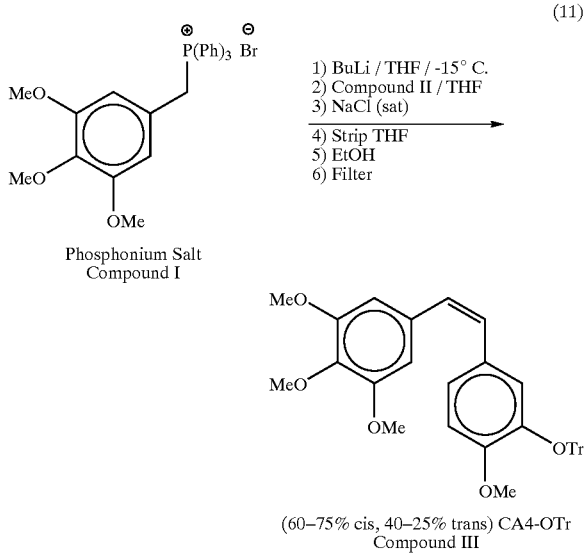

Phosphonium Salt
Compound I

Figure 3:
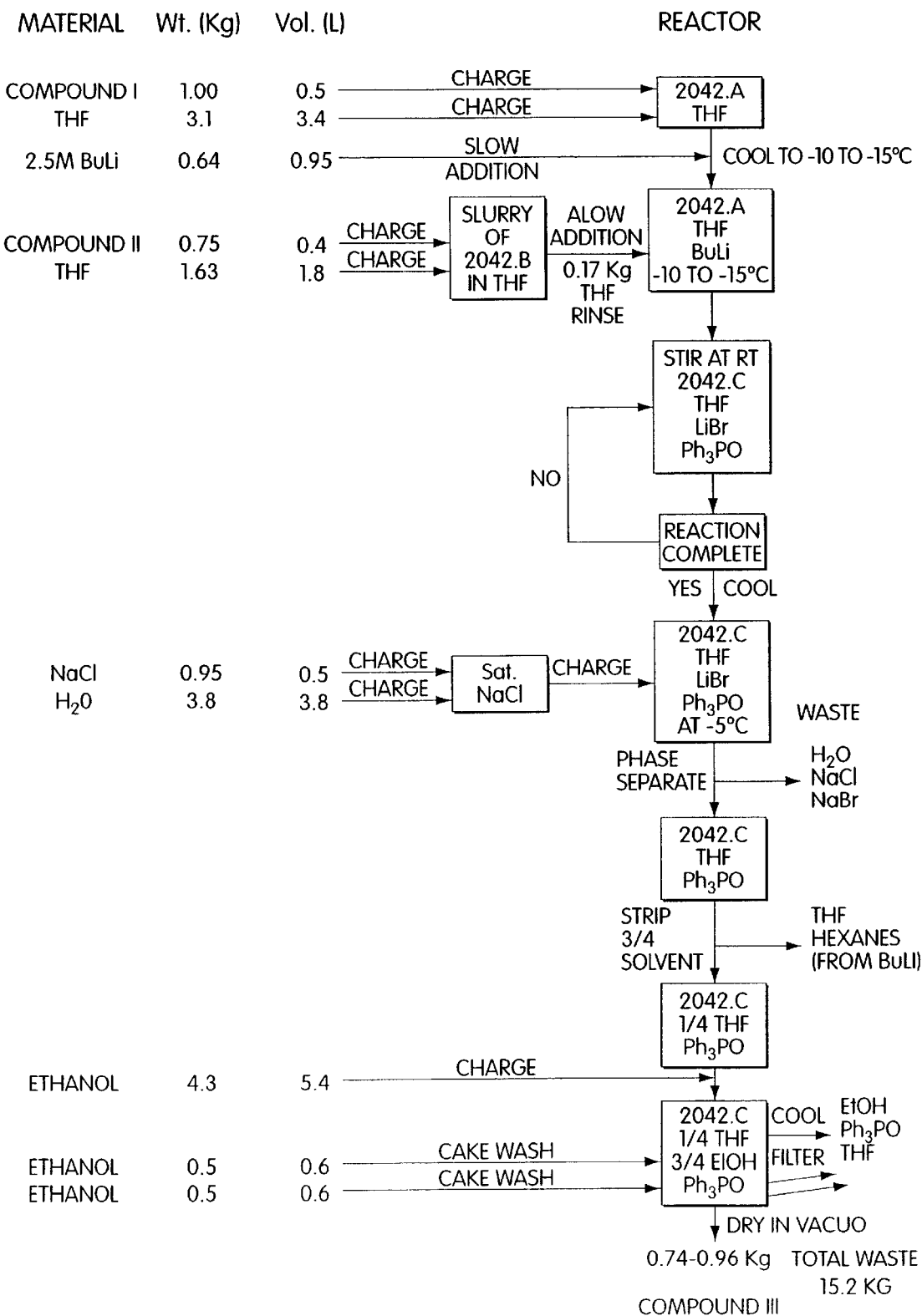
FIG. 3 is a flow chart illustrating the third step in the same specific example.

1) BuLi / THF / -15° C.
2) Compound II / THF
3) NaCl (sat)
4) Strip THF
5) EtOH
6) Filter (60–75% cis, 40–25% trans) CA4-OTr
Compound III and a flow chart of a specific example is shown in FIG. 3.

Step 4 (Detritylation Reaction)

A mixture of Compound III, acid (preferably hydrochloric acid; alternatives include sulfuric acid, hydrobromic acid, methanesulfonic acid, and acid resins such as amberlyst), and toluene is stirred until the reaction is complete. The reaction is quenched with water and the mixture is stirred with cooling. The product is collected, washed and dried to provide exclusively the cis-isomer of combretastatin A-4 (cis-CA4; Compound IV); i.e., only the cis-isomer crystallizes. Step 4 is represented as follows:

(12)

Figure 4:
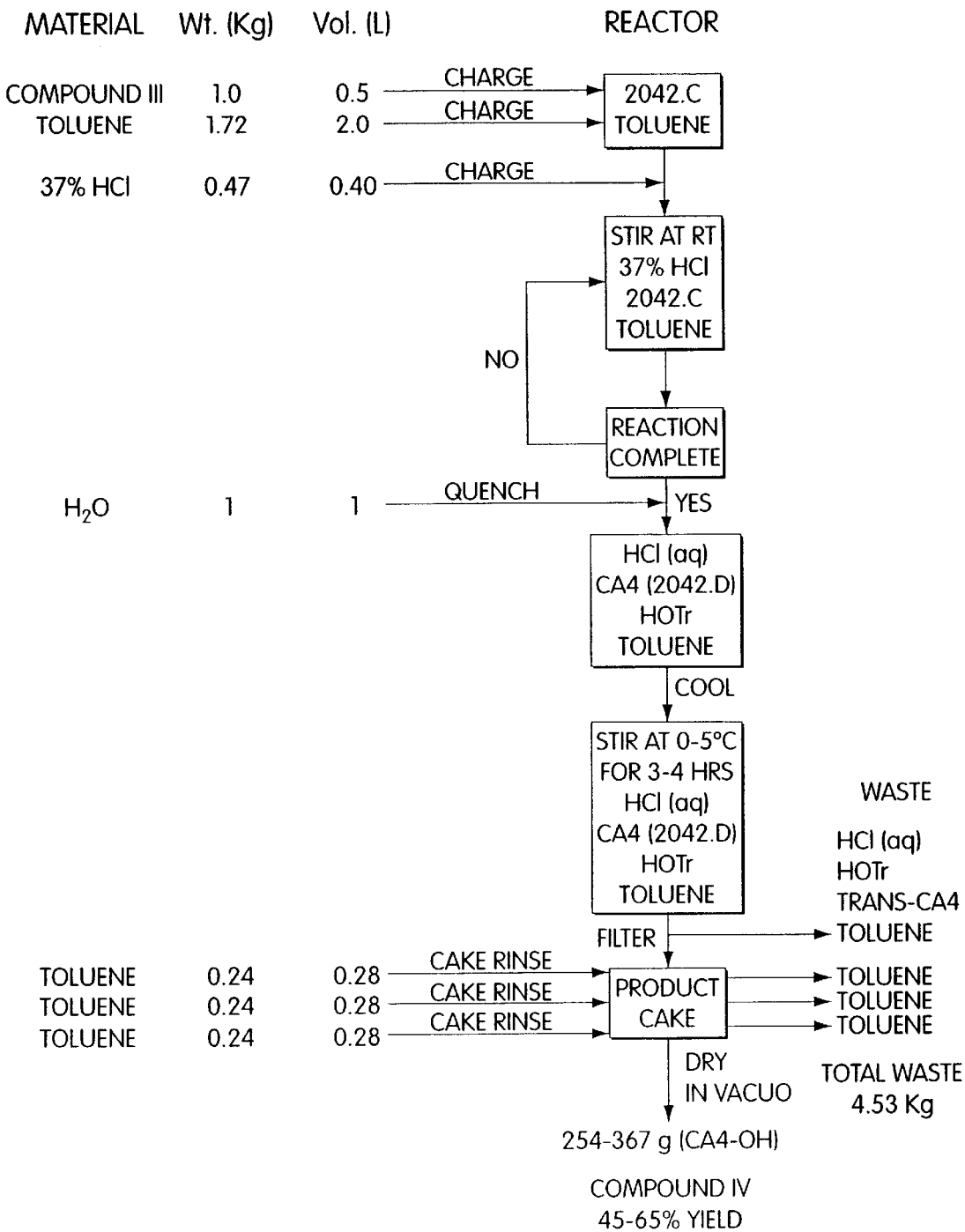
FIG. 4 is a flow chart illustrating the fourth step in the same specific example.

~65% Cis-CA4-OTr
Compound III 1) conc HCl/Toluene
2) water
3) Cool 0–5° C.
4) Filter 100% Cis-CA4-OH
Compound IV and a flow chart of a specific example is shown in FIG. 4.

Prodrug Preparation

Step 5 (Dibenzylphosphorylation Reaction, Deprotection and Disodium Salt Formation)

A cold mixture of the cis-CA4 (Compound IV), a trialkyl amine base (preferably Et$_3$N), CBr$_4$ and acetonitrile (CH$_3$CN) is combined with a mixture of dibenzyl phosphite (HPO(OBn)$_2$) and CH$_3$CN and the resulting mixture is stirred at room temperature until phosphorylation is complete (alternatives to dibenzyl phosphite include, e.g., di-tert butyl phosphite, dibutyl phosphite, diethyl phosphite, diisopropyl phosphite, dimethyl phosphite, diphenyl phosphite, and dipropyl phosphite; together with dibenzyl phosphite, these may be designated phosphites having the formula HPOY$_2$ where Y is benzyl, tert butyl, butyl, ethyl, isopropyl, methyl, phenyl or propyl). Bromotrimethylsilane (TMSBr) is added and the mixture is stirred until debenzylation is complete (alternatives to TMSBr include, e.g., TMSCl/NaBr or NaI, and higher alkyl silyl bromides up to four carbons per alkyl group) or the equivalent higher alkyl silyl chlorides in conjunction with NaBr or NaI; the higher alkyl silyl reagents will react much more slowly in this type of reaction). The reaction is quenched with a solution of sodium methoxide (NaOMe) in methanol (MeOH) and the mixture is stirred (alternatives to NaOMe include, e.g., other sodium alkoxides such as sodium ethoxide, isopropoxide, tert-butoxide and tert amyloxide; sodium 2-ethyl hexanoate, sodium acetate or an ion exchange resin that would act as a sodium carrier). The solid is collected, and washed with acetone to provide a crude product. This crude product is dissolved in a mixture of methanol and water with heat. The solution is basified to pH 10–12 with methanolic sodium methoxide, warmed and diluted with methanol and acetone. The solution is cooled to room temperature; additional acetone is added; and the product is collected and dried to provide the disodium salt of combretastatin A-4 phosphate, CA4P (Compound V). Step 5 is represented as follows:

(13)

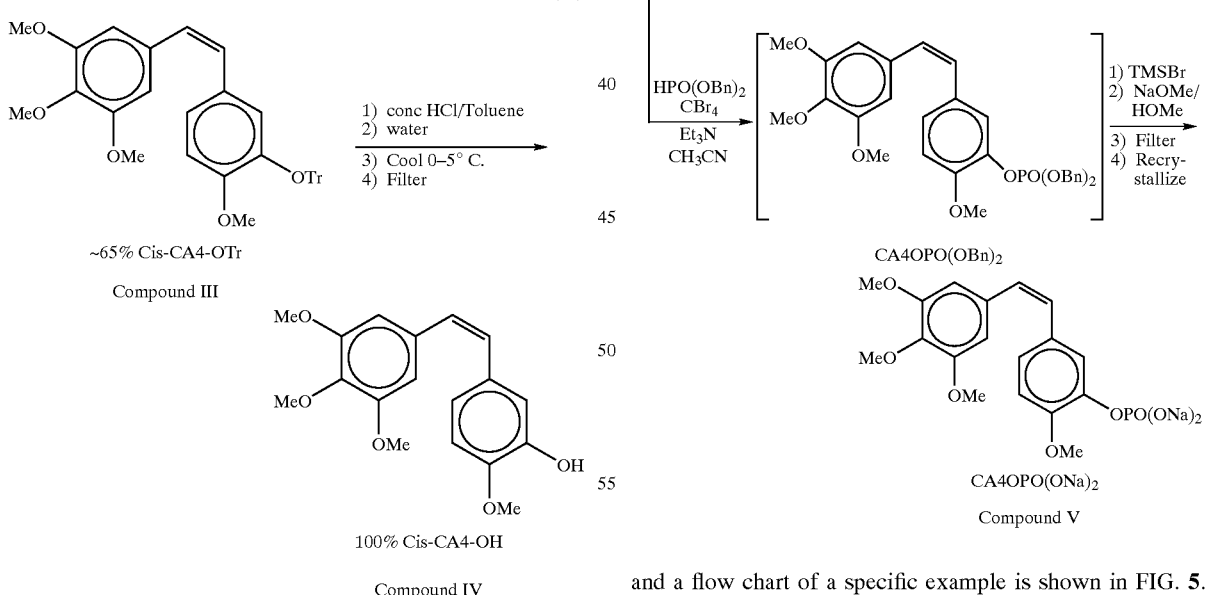

Figure 5:
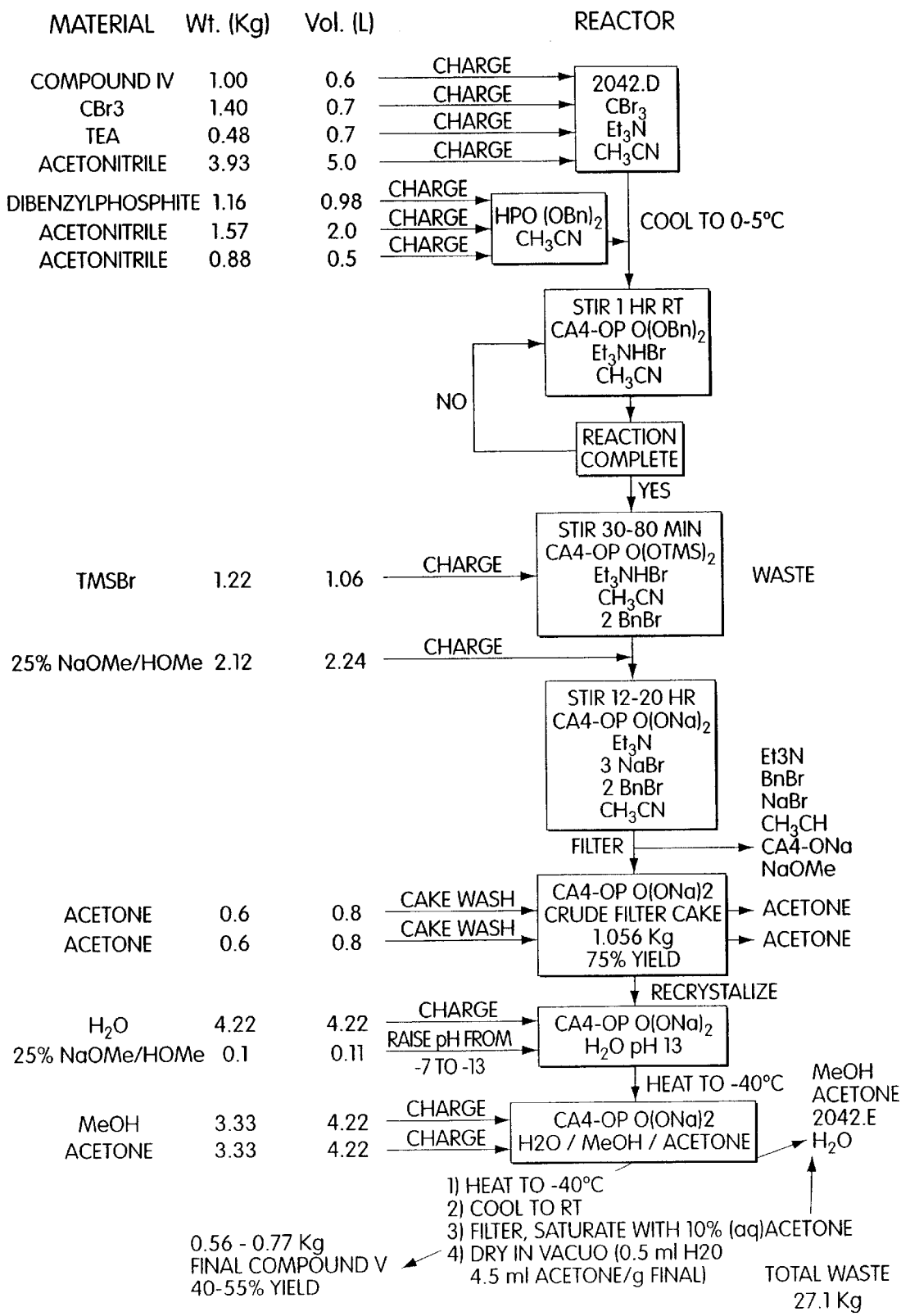
FIG. 5 is a flow chart illustrating the fifth step in the same specific example.

Compound V and a flow chart of a specific example is shown in FIG. 5.

By way of further illustration of the invention, reference may be made to the following specific examples:

EXAMPLE 1

Synthesis of Combretastatin A-4 Prodrugs via Troc Phosphorylation Route

Cis-combretastatin A-4 (5 g, 15.8 mmol, 1 eq) was dissolved in acetonitrile (50 ml) under argon atmosphere and dimethylaminopyridine (50 mg, 0.41 mmol) and bis(2,2,2-trichloroethyl) phosphorochloridate (5.77 g, 21.7, 1.4 eq) were added to the solution forming the phosphate ester of combretastatin A-4. Triethylamine (2.3 g, 22.7, 1.44 eq) was added to the mixture portionwise over 20 minutes. After 30 minutes, TLC confirmed the completion of the reaction. Zinc/copper amalgam (6.26 g) was added to the solution and the solution was heated to 40° C. After 30 minutes, 2,4-pentanedione (1.62 g, 16.2 mmol, 1.02 eq) was added in portions while heating at 40° C. After 1.5 hours, heat was removed and the reaction was cooled to room temperature.

The solution was filtered and washed with acetonitrile (25 ml×2). Water (50 ml) was added to the filtrate and solution was cooled on ice bath and a precipitate formed upon cooling. Dowex ion exchange resin (21 g) was added and ice bath was removed. The mixture turned to a homogeneous orange color suspension. The resin was filtered out and the filtrate was concentrated under reduced pressure to remove most of the acetonitrile. The mixture was dissolved in ethanol and 50% aqueous sodium hydroxide was added to bring the pH to 12–14. The mixture was stirred at room temperature for 30 minutes and filtered with an ethanol rinse (50 ml). In order to purify the product, the crude combretastatin A-4P (2.42 g) was dissolved in ml $H_2O$ Methanol 50% (24 ml) and the solution was filtered to remove any undissolved particles. The solution was then heated to 35–40° C. for 1 hour. Once the solution cooled down to 30° C. acetone was added (12 ml). Solution was allowed to cool to room temperature and stirred for 2 hours. A second volume of acetone was added and the solution was stirred at room temperature for 12–16 hours and the product was filtered out the next day. The cake was washed with 20% $H_2O$/acetone (4.5 ml) twice and then with acetone (4.5 ml). The isolated solid was dried in high-vacuum oven overnight at 40° C.

EXAMPLE 2

Synthesis of Combretastatin A-4 Prodrugs via Benzyl Phosphorylation Route

Cis-combretastatin A-4 (250 g, 791 mmol, 1 eq) was dissolved in acetonitrile (1250 ml). Triethylamine (120 g, 1186 mmol, 1.5 eq) and carbon tetrabromide (320 g, 965 mmol, 1.22 eq) were added to the solution. Dibenzylphosphite (249 g, 949 mmol, 1.2 eq) was dissolved in acetonitrile (500 ml). Reaction was cooled to 0° C. and the dibenzylphosphite solution was added dropwise to the reaction mixture. After one hour, the completion of the reaction was verified by TLC and HPLC. Distilled bromotrimethylsilane (TMS-Br) (306 ml, 2373 mmol, 3 eq) was added to the same mixture. After 30–45 minutes, TLC confirmed completion of the debenzylation, the reaction was quenched with sodium methoxide (25 w % in methanol, 560 ml, 2373 mmol, 3 eq) and allowed to stir overnight. The all cis product was filtered out and washed with 2×400 ml 50% methanol/acetone.

Crude combretastatin A-4P was isolated in approximately 75% yield (85% w/w assay). In order to purify the product, the crude combretastatin A-4P (260 g) was suspended in $H_2O$ (1300 ml). Material dissolved as pH was adjusted to 10–12, using sodium methoxide/methanol (25 w %). Methanol was added to the solution (1300 ml) and the solution was filtered to remove any undissolved particles. The solution was then heated to 35–40° C. for 1 hour. Once the solution cooled down to 30° C. acetone was added (1300 ml). Solution was allowed to cool to room temperature and stirred for 2 hours. A second volume of acetone was added and the solution was stirred at room temperature for 12–16 hours and the product was filtered out the next day. The cake was washed with 20% $H_2O$ acetone (445 ml) twice and then with acetone (445 ml). The isolated solid was dried in high-vacuum oven overnight at 40° C. Combretastatin A-4P was isolated in 40% total yield from starting phenol.

$^1$H NMR $D_2O$, δ3.58 (s, 6H), 3.62 (s, 3H), 3.73 (s, 3H), 4.71 (s, 2H), 6.31 (dd, 2H), 6.70 (quart, 2H), 7.28 (s, 1H). $^{13}$C NMR, D2O δ58.52, 58.74, 63.57, 109.13, 114.96, 124.11, 125.22, 131.45, 132.83, 132.92, 136.35, 138.47, 146.03, 151.84, 151.92, 154.77, pH 8.1–8.5. Na 10.1%. HPLC (AUC) 100%, HPLC (w/w) +99%.

EXAMPLE 3

Comparison of Products

The Compound V product obtained by the specific process example represented by FIG. 5 (herein "Process B") was tested and compared with another sample of combretastatin A-4 disodium phosphate prepared by an earlier and different process (herein "Process A") not embraced within the present invention. It will be noted that Process B (embodying the method of the invention) is also represented by Example 2 above.

The absolute identity (actual disposition of atoms within a unit cell) of these two materials could not be established in the absence of any single crystal x-ray diffraction data on the disodium salt. However, the two materials (Compound V obtained by Process B of the invention, and comparative combretastatin A-4 disodium phosphate obtained by Process B) exhibited physical differences as characterized by DSC, TGA, powder-XRD and solution state $^{13}$CNMR. Results, set forth in Table 4 below, indicate that the product of Process B (of the invention), i.e., Compound V, is a novel product. In Table 4, the comparative product is designated "Process A Product" while Compound V is designated "Process B Product."

TABLE 4

Comparison of Process A and Process B Products

| Property | Process A Product | Process B Product |
|---|---|---|
| Appearance | White powder | White powder |
| Solvent of crystallization | Ethanol | Acetone/methanol/water |
| Microscopy | Irregularly shaped plate-like particles | Agglomerates of irregularly shaped needle-like particles |
| DSC | Endotherm at 110° C. with a shoulder at 77° C. (loss of volatiles) Endotherm max at 267° C. (melting and decomposition) | Endotherm at 122° C. with a shoulder at 74° C. (loss of volatiles) Endotherm max at 258° C. (melting and decomposition) |
| TGA | Weight loss at 150° C. = 4% | Weight loss at 150° C. = 6.2% |
| Moisture sorption at 25° C. | Loss on drying at 1% RH = 5.7% Wt. gain at 30–70% RH = 7–8.6% Wt. gain at > 70% RH = 9–30% | Loss on drying at 1% RH = 6.6% Wt. gain at 30–70% RH = 3% Wt. gain at > 70% RH = upto 30% |
| Powder X-ray diffraction | Low crystallinity Changes X-ray pattern on exposure to different RH conditions Lost its X-ray pattern at extremely low humidity and 100% RH | Low crystallinity, different pattern from that of Process A material |
| Aqueous | pH    Solubility(mg/mL) | pH    Solubility(mg/mL) |

TABLE 4-continued

Comparison of Process A and Process B Products

| Property | Process A Product | | Process B Product | |
|---|---|---|---|---|
| solubility* | 0.6 | 2.27 | 0.80 | 0.21 |
| at 25° C. as | 0.8 | 0.83 | 0.97 | 0.25 |
| a function of | 1.2 | 0.35 | 2.20 | 1.61 |
| pH, pH | 5.2 | 77.4 | 3.26 | 5.35 |
| adjusted | 5.6 | 76.8 | 6.96 | 34.7 |
| with HCl | 7.1 | 169 | 7.28 | 81.2 |
|  | 7.2 | 204 | 7.35 | 94.3 |
|  | 7.8 | 208 | 8.40 | 115 |
|  | 9.4 | 213 (in water) | 9.40 | 118 (in water) |
| Solubility in | Methanol = 22.4 mg/mL | | Methanol = 1.77 mg/mL | |
| organic | Ethanol = 0.18 mg/mL | | Ethanol = 0.096 mg/mL | |
| solvents* at | Acetone = 0.45 mg/mL | | Acetone = BQL$ | |
| 25° C. | | | | |

*solubility values based on cis-CA4P free acid
$BQL = below quantitation limit of the HPLC method used The powder-XRD patterns and the DSC and TGA thermograms of these materials were distinctly different from each other. Also, the initial moisture content for Process B material at the time of analysis was higher than that for Process A material. The Process B product showed consistently lower solubility than the Process A product in both aqueous and organic solvents at 25° C., implying greater stability for the Process B product. The Product A product showed a greater degree of hygroscopicity than the Product B product. Solution state NMR studies showed that there were no chemical differences between the two materials. Based on the available data, it was concluded that Process B afforded a physically more stable material than Process A. Although there are physical differences between the two products, the lyophile drug product prepared from Process B material was in no way compromised for its quality and stability; in fact is was demonstrated to be better than the drug product obtained from Process A material.

It can be appreciated that other salt forms of combretastatin A-4P may be formed by replacing sodium methoxide solution with reactive amounts of alkaline metals or inorganic salts such as $Na^{2+}$, $Na^+$, $Li^+$, $Mg^{2+}$, $Mn^{2+}$, $Zn^{2+}$, $Ca^{2+}$, $Cs^{2+}$, imidazole, morpholine, piperazine, piperidine, pyrazole, pyridine, adenosine, cinchonine, glucosamine, quinine, quinidine, tetracycline, or verapamil resulting in salt forms of combretastatin A-4P with varying solubility.

An advantage of the subject invention is the phosphorylation of the combretastatin A-4 in a continuous process, thereby shortening the reaction from three steps to one step eliminating time consuming and costly work-ups, isolations, purifications, and evaporations.

A further advantage of the subject invention is the development of improved phosphorylation with the benzyl group providing an alternative phosphorylation method to the Troc Method thereby avoiding heavy metal contaminants associated with the deprotection of the Troc group.

A further advantage of the subject invention is the replacement of the ion exchange chromatographic separation of the phosphate acid with an ion exchange resin.

A further advantage of the subject invention is the elimination of carbon tetrachloride, chloroform, DMF and pyridine from the phosphorylation reaction.

A further advantage of the subject invention is the increase in concentration of the reactants thereby allowing increased loading and increasing yield of combretastatin A-4.

A further advantage of the subject invention is elimination of the evaporation of the solvent after the completion of the reaction.

A still further advantage of the subject invention is the elimination of the side products and remaining starting materials during the wash.

The subject invention further provides the advantage of a high throughput, scalable process by eliminating the use of ion exchange chromatography, hazardous and inconvenient solvents and expensive reagents, and by increasing the loading in every step. Consequently, the methods disclosed herein can be scaled up to produce large quantities of combretastatin A-4 prodrugs.

The foregoing is a description of a new, useful and non-obvious method of synthesizing combretastatin A-4 prodrugs.

It is to be understood that the invention is not limited to the features and embodiments hereinabove specifically set forth, but may be carried out in other ways without departure from its spirit.

What is claimed is:

1. A method of synthesizing a phosphate ester of combretastatin A-4 and trans-isomers thereof in which:

combretastatin A-4 having the following chemical structure

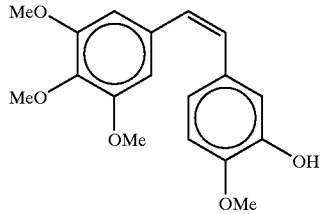

is reacted with dibenzylphosphite in the presence of carbon tetrabromide to form said phosphate ester of combretastatin A-4 with protecting groups thereon.

2. A method of synthesizing a phosphate ester of combretastatin A-4 and trans-isomers thereof in which:

combretastatin A-4 having the following chemical structure:

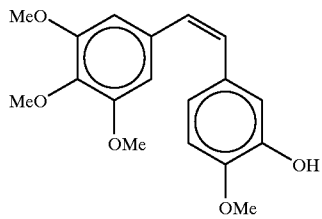

is reacted with (2,2,2-trichloroethyl) phosphorodichloridate in the presence of triethylamine to form said phosphate ester of combretastatin A-4 with protecting groups thereon.

3. A method of synthesizing a phosphoric acid of combretastatin A-4 and trans-isomers thereof in which:

a phosphate ester of combretastatin A-4 with protecting groups thereon having the following chemical structure

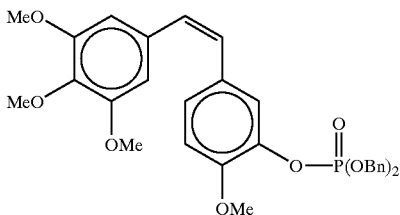

is reacted with bromotrimethylsilane to form said phosphoric acid of combretastatin A-4.

4. A method of synthesizing combretastatin A-4 prodrugs and trans-isomers thereof as phosphate salts comprising:
reacting combretastatin A-4 having the following chemical structure:

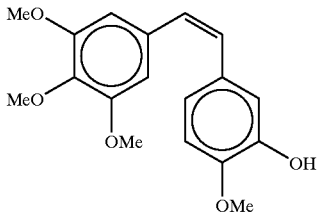

with an activated phosphorylating agent having hydroxyl-protecting groups thereon wherein said phosphorylating agent is either dibenzylphosphite/carbon tetrabromide or bis(2,2,2-trichloroethyl) phosphorodichloridate, in the presence of triethylamine, to form a phosphate ester of combretastatin with protecting groups thereon;
deprotecting said hydroxyl-protecting groups with a deprotecting agent to yield a phosphoric acid of combretastatin A-4; and
reacting said phosphoric acid with reactive agent to form a phosphate salt of combretastatin A-4.

5. The method according to claim 4 wherein the deprotecting agent is bromotrimethylsilane when said phosphorylating agent is dibenzylphosphite/carbon tetrabromide.

6. The method according to claim 4 wherein Zn/Cu amalgam is the deprotecting agent when said phosphorylating agent is(2,2,2-trichloroethyl) phosphorodichloridate in the presence of triethylamine.

7. The method according to claim 4 wherein said phosphoric acid is reacted with sodium methoxide to form a disodium phosphate salt or a monosodium phosphate salt of combretastatin A-4.

8. The method according to claim 4 wherein the said reactive agent is either alkaline metal or inorganic salt.

9. The method according to claim 4 wherein said reactive agent forms X-phosphate salt of combretastatin A-4, wherein X is selected from the group consisting of sodium, cesium, calcium, lithium, magnesium, manganese, potassium, zinc, imidazole, morpholine, piperazine, piperidine, pyrazole, pyridine, adenosine, cinchonine, glucosamine, quinine, quinidine, tetracycline, verapamil.

10. The method of synthesizing combretastatin A-4 prodrugs and trans-isomers thereof comprising:
dissolving combretastatin A-4 in acetonitrile to form a first solution;
admixing triethylamine and carbon tetrabromide in said first solution to form a second solution;
dissolving dibenzylphosphite in acetonitrile to said second solution to form a third solution;
admixing said third solution to said second solution to form a fourth solution; and
admixing bromotrimethylsilane to said fourth solution and treating with sodium methoxide in methanol to form a fifth solution of phosphate salt of combretastatin A-4.

11. The method according claim 10 wherein said phosphate salt is either a monosodium phosphate salt or a disodium phosphate salt of combretastatin A-4.

12. The method according to claim 10 further comprising
isolating the phosphate salt of combretastatin A-4 from said fifth solution to form a crude product;
suspending said crude product in $H_2O$ to form a sixth solution;
treating said sixth solution with sodium methoxide in methanol to form a basic solution;
heating said basic solution to about 35–40° C.; and
admixing acetone to cause said phosphate salt of combretastatin A-4 to recrystalize from said basic solution.

13. In a method of preparing combretastatin A-4 prodrugs and trans-isomers thereof by forming a reaction mixture of combretastatin A-4 with a phosphorylating agent to form a phosphate ester with protecting groups thereon, cleaving said protective groups with a deprotecting agent to form a phosphoric acid derivative of combretastatin A-4 and treating said phosphoric acid with a reactive agent to form a phosphate salt of combretastatin A-4, the improvement of said method wherein:
said phosphorylating agent is either dibenzylphosphite/ carbon tetrabromide or 2,2,2-trichloroethyl) phosphorodichloridate in the presence of triethylamine;
the deprotecting agent is bromotrimethylsilane when said phosphorylating agent is dibenzylphosphite/carbon tetrabromide and Zn/Cu amalgam when said phosphorylating agent is bis(2,2,2-trichloroethyl) phosphorodichloridate in the presence of triethylamine; and
said reactive agent forms X-phosphate salt of combretastatin A-4, wherein X is selected from the group consisting of sodium, cesium, calcium, lithium, magnesium, potassium, zinc, imidazole, morpholine, piperazine, piperidine, pyrazole, pyridine, adenosine, cinchonine, glucosamine, quinine, quinidine, tetracycline and verapamil.

14. The method according to claim 13 further comprising reacting said reaction mixture with triethylamine to form said phosphate ester when the phosphorylating agent is bis(2,2,2-trichloroethyl) phosphorodichloridate.

15. The improvement method according to claim 13 wherein said X-phosphate salt of combretastatin is disodium phosphate.

16. In a method of preparing combretastatin A-4 prodrugs and trans-isomers thereof by treating combretastatin A-4 with a phosphorylating agent to form a phosphate ester of combretastatin A-4 with protecting groups thereon, cleaving said protective groups with a deprotecting agent to form phosphoric acid derivative of combretastatin A-4 and treating said phosphoric acid with an agent to form a salt of combretastatin A-4 phosphate, the improvement of said method wherein:
said combretastatin A-4 is dissolved in acetonitrile, triethylamine and carbon tetrabromide to form a first solution;
adding to said first solution the phosphorylating agent dibenzylphosphite to form a second solution comprising said phosphate ester;

said second solution is treated with the deprotecting agent bromotrimethylsilane to form a phosphoric acid solution; and said phosphoric acid solution is treated with a reactive agent to form X-phosphate salt of combretastatin A-4, wherein X is selected from the group consisting of sodium, cesium, calcium, lithium, magnesium, manganese, potassium, zinc, imidazole, morpholine, piperazine, piperidine, pyrazole, pyridine, adenosine, cinchonine, glucosamine, quinine, quinidine, tetracycline and verapamil.

17. The method according to claim 16 wherein said X-phosphate salt of combretastatin is disodium phosphate to form a disodium phosphate salt of combretastatin A-4.

18. The method according to claim 16 wherein said reactive agent is treated with sodium methoxide to form a disodium phosphate salt of combretastatin A-4.

19. The method according to claim 16 wherein said reactive agent is sodium methoxide to form a basic solution.

20. The method according to claim 16 wherein said basic solution has a pH of about 10–12.

21. The method according to claim 16 wherein said basic solution is further cooled to recrystallize the phosphate salt of combretastatin A-4.

22. A method of synthesizing a combretastatin A-4 prodrug, comprising:

(a) obtaining a phosphonium salt of 3,4,5-trimethoxybenzyl bromide by mixing a brominating reagent and 3,4,5-trimethoxybenzyl alcohol in toluene to obtain said bromide, and adding triphenylphosphine thereto;

(b) obtaining tritylated isovanillin by mixing an amine base, isovanillin, and trityl chloride in an ether solvent, and after quenching, adding heptane and ethyl acetate;

(c) mixing a suspension of said phosphonium salt in tetrahydrofuran, an alkyl lithium reagent, and a slurry of said tritylated isovanillin, to obtain a cis/trans stilbene;

(d) reacting said cis/trans stilbene with an acid to obtain a product consisting essentially of cis combretastatin A-4; and (e) synthesizing a combretastatin A-4 prodrug by reacting said cis combretastatin A-4 with an activated phosphorylating agent having hydroxyl-protecting groups thereon wherein said phosphorylating agent is either dibenzylphosphite/carbon tetrabromide or bis(2,2,2-trichloroethyl) phosphorodichloridate, in the presence of triethylamine, to form a phosphate ester of combretastatin with protecting groups thereon; deprotecting said hydroxyl-protecting groups with a deprotecting agent to yield a phosphoric acid of combretastatin A-4; and reacting said phosphoric acid with reactive agent to form a phosphate salt of combretastatin A-4.

23. A method according to claim 22, wherein the brominating reagent in step (a) is phosphorus tribromide.

24. A method according to claim 22, wherein the triphenylphosphine in step (a) is unsubstituted triphenylphosphine.

25. A method according to claim 22, wherein the amine base in step (b) is triethyl amine.

26. A method according to claim 22, wherein the solvent in step (b) is tetrahydrofuran.

27. A method according to claim 22, wherein the trityl chloride in step (b) is unsubstituted trityl chloride.

28. A method according to claim 22, wherein the alkyl lithium reagent in step (c) is n-butyl lithium.

29. A method according to claim 22, wherein the acid in step (d) is hydrochloric acid.

30. A method according to claim 22, wherein the phosphorylating agent in step (e) is dibenzylphosphite/carbon tetrabromide.

31. A method according to claim 22, wherein the brominating reagent in step (a) is phosphorus tribromide; wherein the triphenylphosphine in step (a) is unsubstituted triphenylphosphine; wherein the amine base in step (b) is triethyl amine; wherein the solvent in step (b) is tetrahydrofuran; wherein the trityl chloride in step (b) is unsubstituted trityl chloride; wherein the alkyl lithium reagent in step (c) is n-butyl lithium; wherein the acid in step (d) is hydrochloric acid; and wherein the phosphorylating agent in step (e) is dibenzylphosphite/carbon tetrabromide.

32. A method of synthesizing combretastatin A-4 prodrugs as phosphate salts comprising reacting combretastatin A-4 with a phosphite having the formula $HPOY_2$ where Y is benzyl, tert butyl, butyl, ethyl, isopropyl, methyl, phenyl or propyl, in the presence of carbon tetrabromide, to form a phosphate ester of combretastatin with protecting groups thereon; deprotecting said hydroxyl-protecting groups with a deprotecting agent to yield a phosphoric acid of combretastatin A-4; and reacting said phosphoric acid with reactive agent to form a phosphate salt of combretastatin A-4.

* * * * *